(12) United States Patent
Flynn et al.

(10) Patent No.: US 11,261,295 B2
(45) Date of Patent: Mar. 1, 2022

(54) POLYGLYCEROL COMPOSITIONS

(71) Applicant: CARGILL, INCORPORATED, Wayzata, MN (US)

(72) Inventors: Ryan L. Flynn, Minneapolis, MN (US); Todd L. Kurth, Maple Grove, MN (US); Christopher P. Stevermer, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 280 days.

(21) Appl. No.: 16/480,619

(22) PCT Filed: Jan. 24, 2018

(86) PCT No.: PCT/US2018/014975
§ 371 (c)(1),
(2) Date: Jul. 24, 2019

(87) PCT Pub. No.: WO2018/140447
PCT Pub. Date: Aug. 2, 2018

(65) Prior Publication Data
US 2019/0352460 A1 Nov. 21, 2019

Related U.S. Application Data

(60) Provisional application No. 62/449,955, filed on Jan. 24, 2017.

(51) Int. Cl.
*C08G 65/34* (2006.01)
*C07D 319/12* (2006.01)

(52) U.S. Cl.
CPC .......... *C08G 65/34* (2013.01); *C07D 319/12* (2013.01)

(58) Field of Classification Search
CPC ......... C07C 41/03; C07C 41/42; C07C 41/26; C07C 43/135; C08G 65/34; C07D 319/12
See application file for complete search history.

(56) References Cited

U.S. PATENT DOCUMENTS

| | | | |
|---|---|---|---|
| 4,960,953 | A | 10/1990 | Jakobson et al. |
| 6,620,904 | B2 | 9/2003 | Lemke |
| 2011/0118508 | A1 | 5/2011 | Soi et al. |
| 2011/0190545 | A1 | 8/2011 | Hoong et al. |
| 2012/0238776 | A1 | 9/2012 | Li et al. |
| 2012/0245398 | A1 | 9/2012 | Lourenco et al. |

FOREIGN PATENT DOCUMENTS

EP 0719752 A1 7/1996

OTHER PUBLICATIONS

PDS-2830-0047, Solvay, Jun. 2008.*

* cited by examiner

*Primary Examiner* — Shane Fang

(57) ABSTRACT

Polyglycerol compositions comprise no more than about 5% by weight of monoglycerol based on non-water ingredients of the polyglycerol composition, and have a combined tetraglycerol and higher polyglycerol content of at least about 55%. Methods of making such compositions from a crude glycerin comprising from 0.01 to 5 wt % of glycerol-containing compounds comprising acetate ester moieties are described.

10 Claims, 1 Drawing Sheet

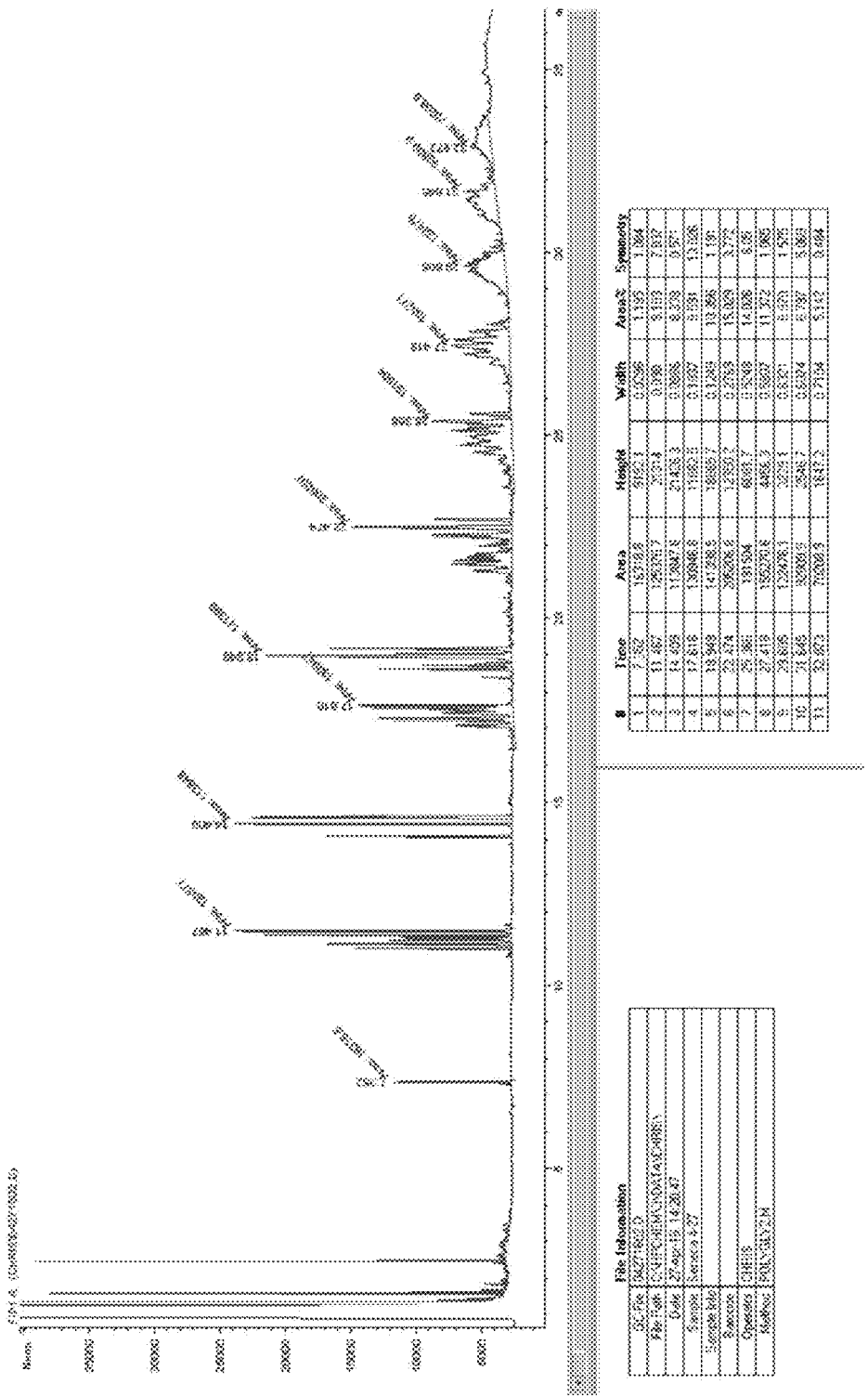

POLYGLYCEROL COMPOSITIONS

CROSS REFERENCE TO RELATED APPLICATIONS

This application is a national phase application of International Application No. PCT/US2018/014975, filed Jan. 24, 2018, entitled POLYGLYCEROL COMPOSITIONS, which claims the benefit of U.S. Provisional Patent Application No. 62/449,955, filed Jan. 24, 2017, entitled POLYGLYCEROL COMPOSITIONS, each of which is hereby incorporated by reference in its entirety.

FIELD

The present invention relates to polyglycerol compositions. More specifically, the present invention relates to polyglycerol compositions comprising unique distributions of glycerol based compounds.

BACKGROUND

Glycerol, which is also called glycerin, is a simple polyol compound that is useful as a sweetener, a humectant, as a cosolvent, and as a starting material for manufacture of a number of products, including polyglycerol polymers. USP Glycerin is monomeric glycerol that satisfies United States Pharmacopeia (USP) requirements. USP Glycerin is readily commercially available.

Polyglycerols are prepared by reacting monoglycerol (also known as "glycerin") under conditions to cause condensation of two or more glycerol molecules. See, for example, U.S. Pat. No. 6,620,904. This reaction produces a glycerol composition comprising a distribution of glycerol based compounds containing various numbers of glycerol units.

SUMMARY

It has been found that particularly beneficial properties may be obtained by polyglycerol compositions comprising a plurality of polyglycerol components in a specific distribution of polyglycerol components. In an aspect, the polyglycerol composition comprises no more than about 5% by weight of monoglycerol based on non-water ingredients of the polyglycerol composition, and has a combined tetraglycerol and higher polyglycerol content of at least about 55%.

In an aspect, a method of making a polyglycerol composition comprising, in order,
a) providing a crude glycerin composition comprising from 0.01 to 5 wt % of glycerol-containing compounds comprising acetate ester moieties;
b) mixing the crude glycerin composition with an excess of potassium hydroxide to acetic acid/ester based on saponification value to form a reaction composition;
c) heating the reaction composition under inert atmosphere in a reactor fitted with a nitrogen sparge, agitation and a distillation condenser to a temperature of from about 220 to 240° C.;
d) reducing the pressure of the reactor at a rate of from about 65 to about 85 torr per hour to a pressure of from about 230 to about 270 Torr;
e) holding the reaction composition at a pressure of from about 230 to about 270 Torr until the glycerin content of the reaction composition as determined by GC is from about 27% to about 33%;
f) reducing the pressure of the reactor at a rate of from about 10 to about 30 torr per hour to a pressure of from about 90 to about 100 torr;
g) holding the reaction composition at a pressure of from about 90 to about 100 torr until the glycerin content of the reaction composition as determined by GC is about 10% or less;
h) reducing the pressure of the reactor at a rate of from about 5 to about 30 torr per hour to a pressure of from about 5 to about 20 torr; and
i) holding the reaction composition at a pressure of from about 5 to about 20 Torr until the glycerin content of the reaction composition as determined by GC is less than 4%.

BRIEF DESCRIPTION OF THE DRAWINGS

The accompanying drawings, which are incorporated in and constitute a part of this application, illustrate several aspects of the invention and together with a description of the embodiments serve to explain the principles of the invention. A brief description of the drawings is as follows:

The FIGURE is GC chromatogram of an aspect of the present polyglycerol.

DETAILED DESCRIPTION

The aspects of the present invention described below are not intended to be exhaustive or to limit the invention to the precise forms disclosed in the following detailed description. Rather a purpose of the aspects chosen and described is by way of illustration or example, so that the appreciation and understanding by others skilled in the art of the general principles and practices of the present invention can be facilitated.

As noted above, polyglycerols are prepared by reacting monoglycerol (also known as "glycerin") under conditions to cause condensation of two or more glycerol molecules. This reaction produces a glycerol composition comprising a distribution of glycerol based compounds containing various numbers of glycerol units, e.g. diglycerol, triglycerol, tetraglycerol, pentaglycerol, and so forth. Cyclic polyglycerols may also be produced, which are polyglycerol compounds where two glycerols in the polyglycerol compound have reacted together form a ring. For purposes of the present disclosure, a "dicyclic" polyglycerol is a diglycerol wherein two glycerols in the polyglycerol compound have reacted together form a ring (i.e. this means that the polyglycerol contains two glycerols in the compound and contains cyclic structure. This does not mean that the compound contains two cyclic structures). For purposes of the present disclosure, a "tricyclic" polyglycerol is a triglycerol wherein two glycerols in the polyglycerol compound have reacted together form a ring (i.e. this means that the polyglycerol contains three glycerols in the compound and contains at least one cyclic structure. This does not mean that the compound contains three cyclic structures). It will be appreciated that the glycerols that react to form the ring are not necessarily adjacent to each other in the polyglycerol compound. The dicyclic and tricyclic polyglycerol compounds are distinguishable from diglycerol and triglycerol compounds that do not contain cyclic functionality by GC analysis. Therefore, dicyclic and tricyclic polyglycerol compounds are not counted in the total amount of diglycerol and triglycerol compounds when reporting relative amounts of polyglycerol components in polyglycerol compositions in the present disclosure.

In preparation of the polyglycerol, a residual amount of monoglycerol will likely if not always be present. For purposes of the present invention, any monoglycerol present in the binder composition will by definition be considered as one of the polyglycerol components of the polyglycerol composition. In an aspect, the polyglycerol composition comprises no more than about 5% by weight of monoglycerol based on non-water ingredients of the polyglycerol composition (i.e. all glycerol based compounds present in the composition). In an aspect, the polyglycerol composition comprises no more than about 2% by weight of monoglycerol. In an aspect, the polyglycerol composition comprises no more than about 1% by weight of monoglycerol. In an aspect, the polyglycerol composition comprises no more than about 0.5% by weight of monoglycerol.

In an aspect, the polyglycerol composition comprises from 0.01 to 5 wt % of glycerol-containing compounds comprising acetate ester moieties. It will be appreciated that any given glycerol-containing compounds comprising acetate ester moieties may comprise one or a plurality of acetate ester moieties.

It has been found that the distribution of glycerol based compounds containing various numbers of glycerol units significantly affects the properties of the resulting binder compositions. In an aspect, the polyglycerol composition has a combined tetraglycerol and higher polyglycerol content of at least about 55%. In an aspect, the polyglycerol composition has a combined tetraglycerol and higher polyglycerol content of from about 58% to about 70%.

In an aspect, the polyglycerol composition has a combined triglycerol and higher polyglycerol content is from about 75% to about 90%. In an aspect, the polyglycerol composition has a triglycerol content of from about 15% to about 30% by weight.

In an aspect, the polyglycerol composition has a combined dicyclic and tricyclic content of at least about 5%. In an aspect, the polyglycerol composition has a combined dicyclic and tricyclic content of at least about 10%. In an aspect, the polyglycerol composition has a combined dicyclic and tricyclic content of at least 15%. In an aspect, the polyglycerol composition has a combined dicyclic and tricyclic content of at least 18%.

In an aspect, the polyglycerol composition comprises less than 200 ppm or less than 150 ppm, or less than 80 ppm, or less than 35 ppm of chloride. In an aspect, the polyglycerol composition comprises less than 200 ppm or less than 150 ppm, or less than 80 ppm, or less than 35 ppm of phosphate. In an aspect, the polyglycerol composition comprises less than 200 ppm or less than 150 ppm, or less than 80 ppm, or less than 35 ppm of sulfate.

In the present method, crude glycerin is provided that comprises from 0.01 to 5 wt % of glycerol-containing compounds comprising acetate ester moieties. This crude glycerin composition is a Biodiesel Sourced Glycerin/Glycerin Acetate that is obtained from a commercial biodiesel process that utilizes acetic acid in the neutralization step. Further, the glycerin/glycerin acetate product used in these examples has been partly refined to attain high glycerin and low free acetic acid. Biodiesel derived "crude glycerol" and uses to make polyglycerol are discussed in U.S. Pat. No. 8,816,133 and EP 0719752. However, the present Biodiesel Sourced Glycerin/Glycerin Acetate is a specific type of crude glycerin due to the presence of glycerin acetate. In an aspect, the present Biodiesel Sourced Glycerin/Glycerin Acetate comprises from about 94 wt % to about 99.8 glycerin, from about 0.1 wt % to about 5 wt % glycerin acetate, and from about 0 wt % to about 1% wt % free acetic acid determined by the AOCS methods Cd3-25, 3d-63, and ASTM D6584.

In an aspect, the Biodiesel Sourced Glycerin/Glycerin Acetate composition may be partially purified, so that it contains no more than 5% acetic acid, contains no more than 0.02% inorganic salt, and/or contains no more than 7% fatty acid.

The Biodiesel Sourced Glycerin/Glycerin Acetate used in the present Examples comprised 95% glycerin, 2.15% glycerin acetate, and 0.3% free acetic acid.

In an aspect, the Biodiesel Sourced Glycerin/Glycerin Acetate composition comprises less than 200 ppm or less than 150 ppm, or less than 80 ppm, or less than 35 ppm of chloride. In an aspect, the Biodiesel Sourced Glycerin/Glycerin Acetate composition comprises less than 200 ppm or less than 150 ppm, or less than 80 ppm, or less than 35 ppm of phosphate. In an aspect, the Biodiesel Sourced Glycerin/Glycerin Acetate composition comprises less than 200 ppm or less than 150 ppm, or less than 80 ppm, or less than 35 ppm of sulfate.

This crude glycerin is mixed with an excess of potassium hydroxide to acetic acid/ester based on saponification value to form a reaction composition. In an aspect, the crude glycerin is mixed with from about 1.02 to about 1.2 molar equivalent of potassium hydroxide to 1 mole acetic acid/ester based on saponification value. In an aspect, the crude glycerin is mixed with from about 1.04 to about 1.08 molar equivalent of potassium hydroxide to 1 mole acetic acid/ester based on saponification value.

The reaction composition is heated under inert atmosphere in a reactor fitted with an inert atmosphere sparge, agitation and a distillation condenser to a temperature of from about 220 to 240° C. In an aspect, the inert atmosphere is nitrogen.

The pressure of the reactor is reduced at a rate of from about 65 to about 85 torr per hour to a pressure of from about 230 to about 270 Torr. In an aspect, the pressure of the reactor is reduced at a rate of from about 70 to about 80 torr per hour.

The reaction composition is then held at a pressure of from about 230 to about 270 torr until the glycerin content as determined by GC is from about 27% to about 33%.

The pressure of the reactor is then reduced at a rate of from about 10 to about 30 torr per hour to a pressure of from about 90 to about 100 torr. In an aspect, the pressure of the reactor is reduced at a rate of from about 15 to about 25 torr per hour.

The reaction composition is then held at a pressure of from about 90 to about 100 torr until the glycerin content of the reaction composition is about 10% or less.

The pressure of the reactor is then reduced at a rate of from about 5 to about 30 torr per hour to a pressure of from about 5 to about 20 torr.

The reaction composition is then held at a pressure of from about 5 to about 20 Torr until the glycerin content of the polyglycerol composition is less than 4%. In an aspect, the reaction composition is held at a pressure of from about 5 to about 20 Torr until the glycerin content of the polyglycerol composition is less than 2%.

The product made by any of the methods described herein is also contemplated as an aspect of the present invention.

The above described polyglycerol composition may be used as additives, such as for use in cosmetics and the like, and as intermediates for further reaction products, such as binder compositions. In an aspect, the above described polyglycerol composition may be used to prepare a binder composition to prepare nonwoven products, such as a fibrous insulation product comprising a plurality of randomly oriented fibers. In an aspect, the above described polyglycerol composition may be used as shale inhibitors for oilfield, de-dust fluids, sizing agents, industrial and in food applications.

EXAMPLES

I. Glycerin Sources

Biodiesel Sourced Glycerin/glycerin acetate is obtained from a commercial biodiesel process that utilizes acetic acid in the neutralization step. Further, the glycerin/glycerin acetate product used in these examples has been partly refined to attain high glycerin and low free acetic acid. This process results in a composition that comprises a significant level of glycerol-containing compounds comprising acetate ester moieties. Biodiesel derived "crude glycerol" and uses to make polyglycerol are discussed in U.S. Pat. No. 8,816,133 and EP 0719752. However, the present Biodiesel Sourced Glycerin/Glycerin Acetate is a specific type of crude glycerin due to the presence of glycerin acetate. In an aspect, the present Biodiesel Sourced Glycerin/Glycerin Acetate comprises from about 94 wt % to about 99.8 glycerin, from about 0.1 wt % to about 5 wt % glycerin acetate, and from about 0 wt % to about 1% wt % free acetic acid determined by the AOCS methods Cd3-25, 3d-63, and ASTM D6584.

In an aspect, the Biodiesel Sourced Glycerin/Glycerin Acetate composition may be partially purified, so that it contains no more than 5% acetic acid, contains no more than 0.02% inorganic salt, and/or contains no more than 7% fatty acid.

The Biodiesel Sourced Glycerin/Glycerin Acetate used in the present Examples comprised 95% glycerin, 2.15% glycerin acetate, and 0.3% free acetic acid.

II Polyglycerol Composition Syntheses

A number of polyglycerol compositions were prepared having a distribution of glycerol based compounds containing various numbers of glycerol units. The polyglycerol compositions prepared, and the distribution of glycerol based compounds in these compositions as determined by GC as described below are presented in Table 1 below:

TABLE 1

| Components (%) | Polyglycerol I | Polyglycerol II |
| --- | --- | --- |
| gly | 1.2% | 3.5% |
| dicyclic | 9.2% | 12.9% |
| di- | 8.3% | 7.9% |
| tricyclic | 9.6% | 7.1% |
| tri- | 10.4% | 9.7% |
| tetra- | 15.0% | 14.0% |
| penta- | 14.0% | 11.8% |
| hexa- | 11.4% | 9.5% |
| hepta-+ | 20.9% | 23.6% |
| Sum | 100% | 100.0% |

The specific manner of preparing these polyglycerol compositions is described as follows:

Polyglycerol I:

Biodiesel Sourced Glycerin/Glycerin Acetate is loaded into a reactor with a 1.05:1 molar equivalent of potassium hydroxide to acetic acid/ester based on saponification value. The reactor was set up with a nitrogen sparge, agitation and a distillation condenser. The reactor is heated to 230° C. with nitrogen sparge. Once 230° C. is reached, the nitrogen sparge is shut off and the reactor is gradually brought down to 250 Torr at a rate of about 75 Torr per hour. When 250 Torr is reached, the reaction is monitored via GC until the glycerin content of the polyglycerol composition is between 27% and 33%. Then vacuum is walked down to 100 Torr at a rate of 20 Torr per hour. The reactor pressure is held at 100 Torr until the glycerin content as determined by GC is about 8% or less. The reactor pressure is then reduced at a rate of 10 Torr per hour to a pressure of 10 Torr, and the reaction is held at 10 Torr until the glycerin content of the polyglycerol component is less than 4%. Once this is achieved, the vacuum is stopped and the reactor is re-pressurized under nitrogen and the reactor is cooled.

Polyglycerol II:

Biodiesel Sourced Glycerin/Glycerin Acetate is loaded into a reactor with a 1.05:1 molar equivalent of potassium hydroxide to acetic acid/ester based on saponification value. The reactor was set up with a nitrogen sparge, agitation and a distillation condenser. The reactor is heated to 230° C. with nitrogen sparge. Once 230° C. is reached, the nitrogen sparge is shut off and the reactor is gradually brought down to 250 Torr at a rate of about 75 Torr per hour. When 250 Torr is reached, the reaction is monitored via GC until the glycerin content of the polyglycerol composition is between 27% and 33%. Then vacuum is walked down to 100 Torr at a rate of 20 Torr per hour. The reactor pressure is held at 100 Torr until the glycerin content as determined by GC is about 8% or less. The reactor pressure is then reduced at a rate of 10 Torr per hour to a pressure of 10 Torr, and the reaction is held at 10 Torr until the glycerin content of the polyglycerol component is less than 4%. Once this is achieved, the vacuum is stopped and the reactor is re-pressurized under nitrogen and the reactor is cooled.

Note that the component distribution of Polyglycerol I is different from that of Polyglycerol II. Such batch to batch variance is expected in small scale experimental Polyglycerol preparation.

GC Method:

Samples were analyzed using an Agilent 6890 GC with a 30 m DB-5HT column and flame ionization detector (FID) with injector and detector temperatures of 375° C. The oven was initially set to 80° C., then ramped at 10° C./min to 350 and held for 10 minutes. Hydrogen was the carrier gas with flow set at 30 ml/min with air flow of 300 ml/min and nitrogen purge of 30 ml/min and a 20:1 split. Samples were derivatized in pyridine using BSTFA (N,O-Bis(trimethylsilyl)trifluoroacetamide), then further diluted using toluene before injection. Glycerin content of samples is determined by the above described method, using a calibration plot and trimethylolpropane (TMP) as an internal standard.

Chromatographic peak data are integrated and interpreted vs % area assuming all components have the same response factor. Values are based on a % weight. Typical retention times for the components of the polyglycerol composition are presented in Table 2:

TABLE 2

| Component | Typical Retention Time (min) |
| --- | --- |
| Glycerin | 7-8 |
| Dicyclic glycerin | 11-12 |
| diglycerin | 14-15 |
| Tricyclic glycerin | 17-18 |
| triglycerin | 18-19 |
| tetraglycerin | 21-23 |
| pentaglycerin | 24-26 |
| hexaglycerin | 27-28 |

TABLE 2-continued

| Component | Typical Retention Time (min) |
|---|---|
| Heptaglycerin | 29-30 |
| Octylglycerin | 31-32 |
| Nonaglycerin | 33-34 |

It will be understood that retention times can shift from instrument to instrument based on slight variations on GC flows and pressures.

FIG. 1 is a GC chromatogram of Polyglycerol I. The calculated composition distribution of the average of the distributions of Polyglycerol I and Polyglycerol II is shown in Table 3.

TABLE 3

| Component | % |
|---|---|
| Glycerin | 2.35 |
| Dicyclic glycerin | 11.05 |
| diglycerin | 8.1 |
| Tricyclic glycerin | 8.35 |
| triglycerin | 10.05 |
| tetraglycerin | 14.5 |
| pentaglycerin | 12.9 |
| hexaglycerin | 10.45 |
| Hepta + glycerin | 22.3 |

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Examples of such limitations include preparing the sample in a wet versus a dry environment, different instruments, variations in sample height, and differing requirements in signal-to-noise ratios. For example, "about" can mean greater or lesser than the value or range of values stated by 1/10 of the stated values, but is not intended to limit any value or range of values to only this broader definition. For instance, a concentration value of about 30% means a concentration between 27% and 33%. Each value or range of values preceded by the term "about" is also intended to encompass the embodiment of the stated absolute value or range of values. Alternatively, particularly with respect to biological systems or processes, the term can mean within an order of magnitude, preferably within 5-fold, and more preferably within 2-fold, of a value.

Throughout this specification and claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein "consisting of" excludes any element, step, or ingredient not specified in the claim element. When used herein, "consisting essentially of" does not exclude materials or steps that do not materially affect the basic and novel characteristics of the claim. In the present disclosure of various embodiments, any of the terms "comprising", "consisting essentially of" and "consisting of" used in the description of an embodiment may be replaced with either of the other two terms.

All patents, patent applications (including provisional applications), and publications cited herein are incorporated by reference as if individually incorporated for all purposes. Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A polyglycerol composition comprising a plurality of polyglycerol components,
wherein the polyglycerol composition comprises from 0.01 to 5 wt % of glycerol-containing compounds comprising acetate ester moieties,
the polyglycerol composition comprises no more than about 5% by weight of monoglycerol based on non-water ingredients of the polyglycerol composition, and
a combined tetraglycerol and higher polyglycerol content of at least about 55%.

2. The polyglycerol composition of claim 1, wherein the polyglycerol composition comprises no more than about 2% by weight of monoglycerol based on non-water ingredients of the polyglycerol composition.

3. The polyglycerol composition of claim 1, wherein the combined tetraglycerol and higher polyglycerol content is from about 58% to about 70%.

4. The polyglycerol composition of claim 1, wherein the combined triglycerol and higher polyglycerol content is from about 75% to about 90%.

5. The polyglycerol composition of claim 2, wherein the polyglycerol composition has a combined triglycerol and tricyclic polyglycerol content of from about 15% to about 30% by weight.

6. The polyglycerol composition of claim 1, wherein the polyglycerol composition has a combined dicyclic and tricyclic content of at least about 5%.

7. The polyglycerol composition of claim 2, wherein the polyglycerol composition has a combined dicyclic and tricyclic content of at least about 10%.

8. The polyglycerol composition of claim 1, wherein the polyglycerol composition has a combined dicyclic and tricyclic content of at least about 15%.

9. The polyglycerol composition of claim 1, wherein the polyglycerol composition has a combined dicyclic and tricyclic content of at least about 18%.

10. The polyglycerol composition of claim 1, wherein the polyglycerol composition comprises less than 200 ppm of each of chloride, phosphate or sulfate.

* * * * *